(12) United States Patent
Shen et al.

(10) Patent No.: US 7,828,019 B2
(45) Date of Patent: Nov. 9, 2010

(54) FABRIC FOR DETECTING VITAL SIGNALS FROM HUMAN BODY

(75) Inventors: Chien-Lung Shen, Chiayi (TW); Kun-Chuan Tsai, Banciao (TW); Ching-Tang Huang, Sindian (TW); Chen-Ta Yin, Tu-Chen (TW)

(73) Assignee: Taiwan Textile Research Institute, Tu-Chen, Taipei Hsien (TW)

( * ) Notice: Subject to any disclaimer, the term of this patent is extended or adjusted under 35 U.S.C. 154(b) by 189 days.

(21) Appl. No.: 12/228,318

(22) Filed: Aug. 12, 2008

(65) Prior Publication Data

US 2009/0277528 A1 Nov. 12, 2009

(30) Foreign Application Priority Data

May 8, 2008 (TW) .............................. 97117041 A

(51) Int. Cl.
*D03D 13/00* (2006.01)
*D03D 11/00* (2006.01)
*D03D 15/00* (2006.01)

(52) U.S. Cl. .............................. 139/383 R; 139/420 R; 139/425 R; 139/426 R

(58) Field of Classification Search ............. 139/383 R, 139/420 R, 408–414, 421, 422, 423, 425 R, 139/426 R, 420 A
See application file for complete search history.

(56) References Cited

U.S. PATENT DOCUMENTS

| 3,067,779 | A | * | 12/1962 | Draper, Jr. | ............... | 139/383 R |
| 3,364,402 | A | * | 1/1968 | Davis | ............... | 139/420 R |
| 4,557,968 | A | * | 12/1985 | Thornton et al. | ............ | 442/198 |
| 4,926,910 | A | * | 5/1990 | Wade | ..................... | 139/425 R |
| 5,802,607 | A | * | 9/1998 | Triplette | ............................ | 2/1 |
| 6,210,771 | B1 | * | 4/2001 | Post et al. | .................... | 428/100 |
| 2001/0047992 | A1 | * | 12/2001 | DeAngelis et al. | .......... | 219/529 |
| 2002/0180578 | A1 | * | 12/2002 | Sandbach | ..................... | 338/99 |
| 2006/0111640 | A1 | * | 5/2006 | Shen et al. | .................. | 600/509 |
| 2006/0211934 | A1 | | 9/2006 | Hassonjee et al. | | |
| 2007/0078324 | A1 | | 4/2007 | Wijisiriwardana | | |
| 2007/0089800 | A1 | | 4/2007 | Sharma | | |
| 2007/0215232 | A1 | * | 9/2007 | Hassonjee et al. | ........ | 139/425 R |
| 2007/0246120 | A1 | * | 10/2007 | Krobok et al. | ............. | 139/421 |
| 2008/0202623 | A1 | * | 8/2008 | DeAngelis et al. | ...... | 139/425 R |

FOREIGN PATENT DOCUMENTS

| EP | 1661512 A1 * | 5/2006 |
| TW | 200701947 | 1/2007 |

\* cited by examiner

*Primary Examiner*—Bobby H Muromoto, Jr.
(74) *Attorney, Agent, or Firm*—Kinney & Lange, P.A.

(57) ABSTRACT

A fabric for detecting vital signals from human body includes a layer of fabric and electrically conductive yarns. The layer of fabric is formed of weft and warp electrically insulating yarns woven together. Electrically conductive yarns is woven in parallel with weft or warp electrically insulating yarns and interval-spaced from one another. Each of the electrically conductive yarns has a wave-shaped detecting section. All wave crests of the wave-shaped detecting section are protruded out of a surface of the layer of fabric while all wave troughs of the wave-shaped detecting section are woven within the layer of fabric. Each of electrically conductive yarns has its all wave crests misaligned in position with all wave crests of its immediately adjacent electrically conductive yarn. Each of electrically conductive yarns has its all wave troughs misaligned in position with all wave troughs of its immediately adjacent electrically conductive yarn.

20 Claims, 7 Drawing Sheets

FABRIC FOR DETECTING VITAL SIGNALS FROM HUMAN BODY

RELATED APPLICATIONS

This application claims priority to Taiwan Application Serial Number 97117041, filed May 8, 2008, which is herein incorporated by reference.

BACKGROUND

1. Field of Invention

The present invention relates to a woven fabric. More particularly, the present invention relates to a woven fabric for detecting vital signals from human body.

2. Description of Related Art

Conventional electrodes for detecting electrocardiogram signal (ECG), Eye on Gambling (EOG), Electroencephalogram (EEG) or electromyogram (EMG) are integrated within a tape, which is attached on a human skin. When such tape electrode is attached on a human skin for a long time period, the human skin itches or gets any irritating sensation due the tape electrode, which is not porous.

For the forgoing reasons, there is a need for improving the conventional electrodes for detecting vital signals from human body.

SUMMARY

It is therefore an objective of the present invention to provide a fabric for detecting vital signals from human body.

In accordance with the foregoing and other objectives of the present invention, a fabric for detecting vital signals from human body includes a layer of fabric and electrically conductive yarns. The layer of fabric is formed of weft and warp electrically insulating yarns woven together. Electrically conductive yarns is woven in parallel with weft or warp electrically insulating yarns and interval-spaced from one another. Each of the electrically conductive yarns has a wave-shaped detecting section. All wave crests of the wave-shaped detecting section are protruded out of a surface of the layer of fabric while all wave troughs of the wave-shaped detecting section are woven within the layer of fabric. Each of electrically conductive yarns has its all wave crests misaligned in position with all wave crests of its immediately adjacent electrically conductive yarn. Each of electrically conductive yarns has its all wave troughs misaligned in position with all wave troughs of its immediately adjacent electrically conductive yarn.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
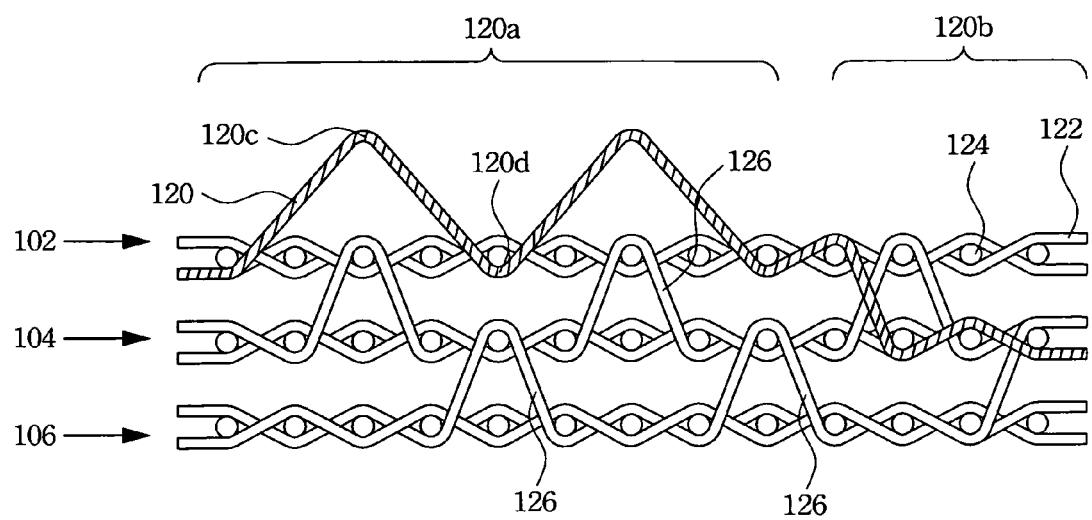
FIG. 1 illustrates a cross-sectional view of a fabric for detecting vital signals from human body according to one preferred embodiment of this invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 illustrates a cross-sectional view of a fabric for detecting vital signals from human body according to one preferred embodiment of this invention. A fabric 100 includes three layers: a first layer 102, a second layer 104 and a third layer 106. Three layers of fabric (102, 104, 106) consists mainly of electrically insulating yarns (122, 124) woven as weft and warp yarns thereof and an electrically insulating yarn 126 is used to weave three layers together. In order to detect vital signals from human body, an electrically conductive yarn 120 is also woven into the fabric 100. The electrically conductive yarn 120 includes a detecting section 120a and a transferring section 120b. The detecting section 120a is woven into the first layer 102 as a wave-shaped section. The detecting section 120a has all wave crests 120c sticking out of a surface of the first layer 102 for directly contacting human skins. The detecting section 120a has all wave troughs 120d woven within the first layer 102. The transferring section 120b is woven within the second layer 104. Because the second layer 104 is sandwiched between the first layer 102 and the third layer 106, the transferring section 120b, which is woven within the second layer 104, is electrically isolated from outer environments and able to transfer vital signals to a measuring instrument (not illustrated in drawings).

In this preferred embodiment, the detecting section 120a is woven with the first layer 102 by "one unit down and three units up" weaving way. By "one unit down and three units up", it means that "after the detecting section 120a has its wave trough 120d woven with one electrically insulating yarn 124, the detecting section 120a sticks out of the first layer 102, goes beyond three electrically insulating yarns 124, and then has its next wave trough 120d woven with the first layer 102 again. Thus, detecting section 120a has any immediately adjacent two wave troughs 120d disposed with the three electrically insulating yarns 124 therebetween. By "one unit down and three units up" weaving way, the detecting section 120a, which sticks out of the first layer 102, can be limited within a desired range. The longer the detecting section 120a sticks out of the first layer 102, the more contact area for detecting vital signals the detecting section 120a may have, but the longer detecting section 120a may has its fibers damaged more easily due to being washed or in contact with human skins. "One unit down and three units up" is a better weaving way to control the sticking-out detecting section 120a to such a length that it will not be damaged due to being washed or in contact with human skins. However, it does not mean that other weaving ways is not proper for the present preferred embodiments, such as "one unit down and one unit up" or "one unit down and five units up".

In addition, in order to make the detecting section 120a in contact with human skins firmly, the electrically insulating yarns 122, which are in parallel with the electrically conductive yarns 120, have a larger linear elasticity than that of the electrically insulating yarns 124, which are not in parallel with the electrically conductive yarns 120 in three layers of fabric (102, 104, 106). In present invention, the electrically insulating yarns 122 with a larger linear elasticity is able to maintain the detecting section 120a sticking out the first layer 102.

Figure 2:
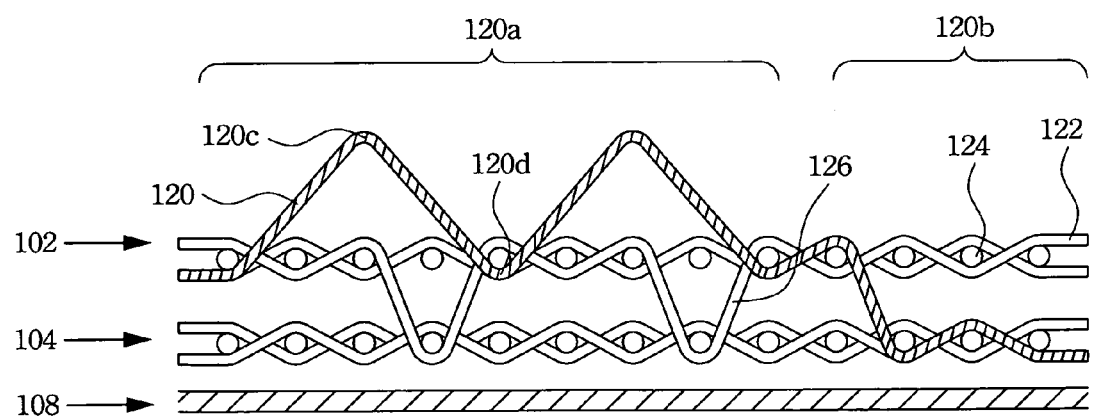
FIG. 2 illustrates a cross-sectional view of a fabric for detecting vital signals from human body according to another preferred embodiment of this invention.

FIG. 2 illustrates a cross-sectional view of a fabric for detecting vital signals from human body according to another preferred embodiment of this invention. This preferred embodiment consists of two layers of fabric (102, 104) plus an electrically insulating layer 108. This preferred embodiment has the same features as the preferred embodiment illustrated in FIG. 1 except that the third layer of fabric 106 is replaced by the electrically insulating layer 108. The electrically insulating layer 108 is not a woven fabric. The third layer of fabric 106 (as illustrated in FIG. 1) serves as an electrically insulating shielding, and thus can be replaced by any electrically insulating layer, which is not a woven fabric. The electrically insulating layer 108 may also have air vents (not illustrated in drawings) to be porous.

Figure 3:
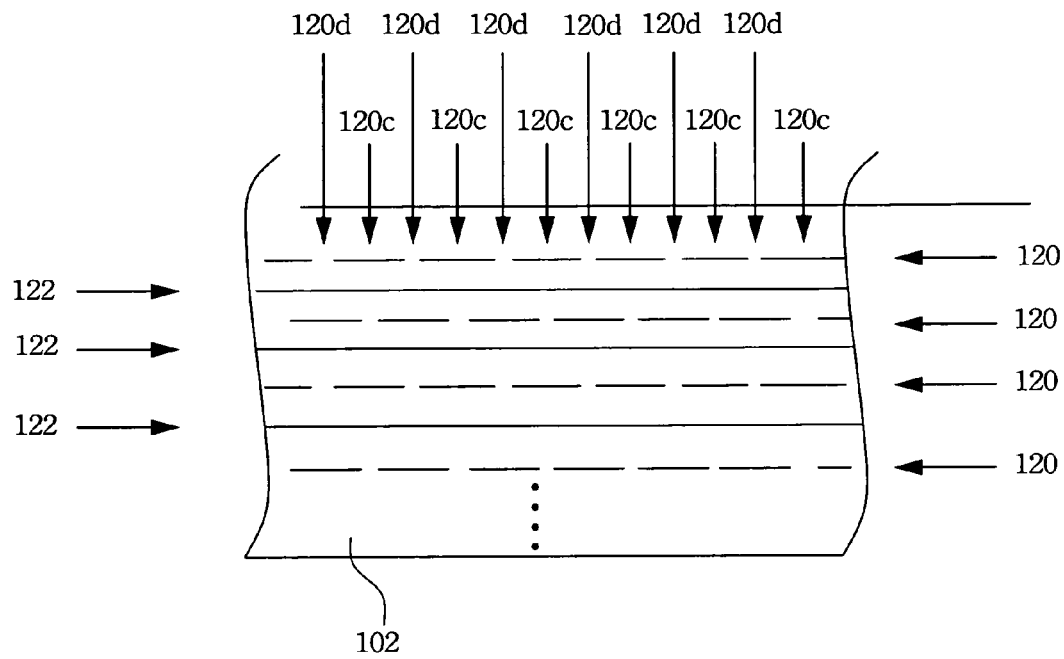
FIG. 3 illustrates a top view of a fabric for detecting vital signals from human body as in FIG. 1 or FIG. 2.

FIG. 3 illustrates a top view of a fabric for detecting vital signals from human body as in FIG. 1 or FIG. 2. In order to have an optimum fabric 100 for detecting vital signals from human body, the detecting sections 120a had better not be overlapped by one another, especially the detecting sections of two adjacent electrically conductive yarns. Because overlapped detecting sections 120a would decrease contact area for detecting vital signals, less vital signals may be collected from human skins. In present preferred embodiments, the detecting sections 120a has its wave crests or wave troughs misaligned with one another so as to reduce overlapped detecting sections. For instances, each of the electrically conductive yarn has its all wave crests 120c (of the detecting sections 120a) misaligned in position with all wave crests 120c of its immediately adjacent electrically conductive yarn, and each of electrically conductive yarns has its all wave troughs 120d (of the detecting sections 120a) misaligned in position with all wave troughs 120d of its immediately adjacent electrically conductive yarn. In FIG. 3, each of electrically conductive yarns has its all wave crests 120c (of the detecting sections 120a) aligned in position with all wave troughs 120d of its immediately adjacent electrically conductive yarn. Besides, any immediately adjacent two of electrically conductive yarns 120 have at least one electrically insulating yarn 122 disposed therebetween.

Figure 4:
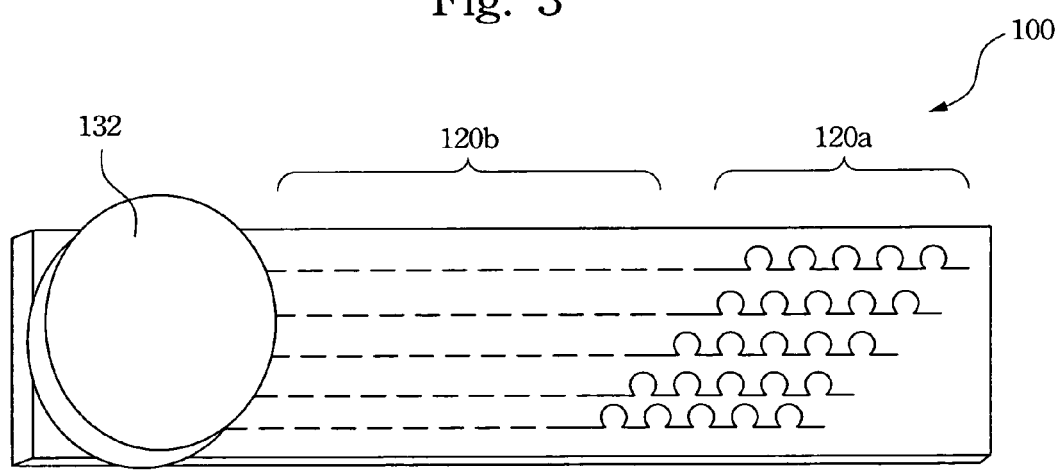
FIGS. 4~6 illustrate three different electrodes to electrically connect with the fabric for detecting vital signals from human body.
Figure 5:
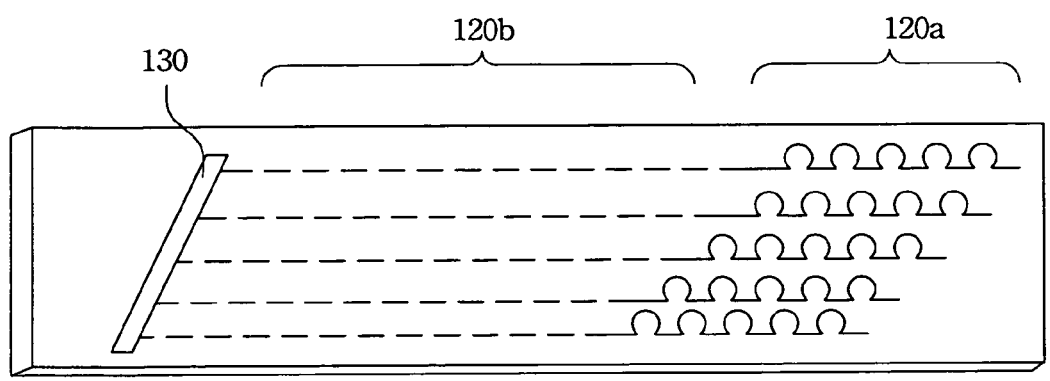
Figure 6:
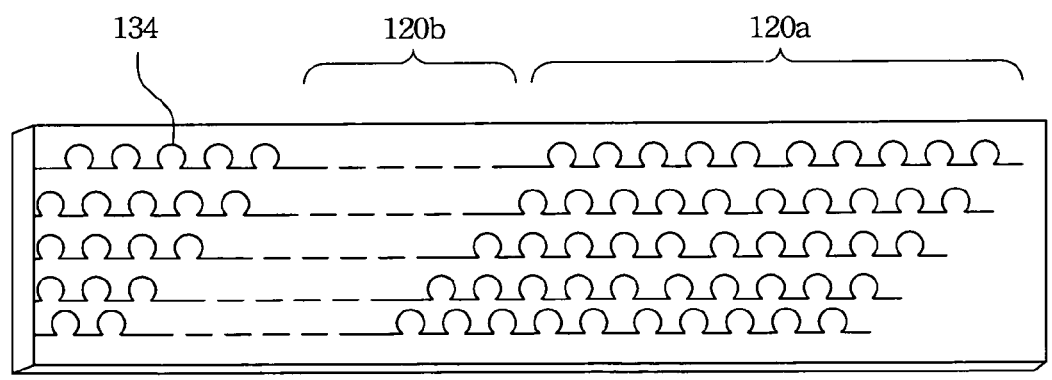

FIGS. 4~6 illustrate three different electrodes to electrically connect with the fabric for detecting vital signals from human body. Vital signals, which are collected by detecting sections 120a of the fabric 100, should be transferred to a measuring instrument (not illustrated in drawings) by the transferring section 120b. An intermediate electrode is necessary to interconnect the transferring section 120b and the measuring instrument. In FIG. 4, the intermediate electrode 132 is a metallic button. In FIG. 5, the intermediate electrode 130 is a metal bar. In FIG. 6, the intermediate electrode 134 is an area having the same structure as the detecting section 120a, upon which a connector of the measuring instrument is pressed.

Figure 7:
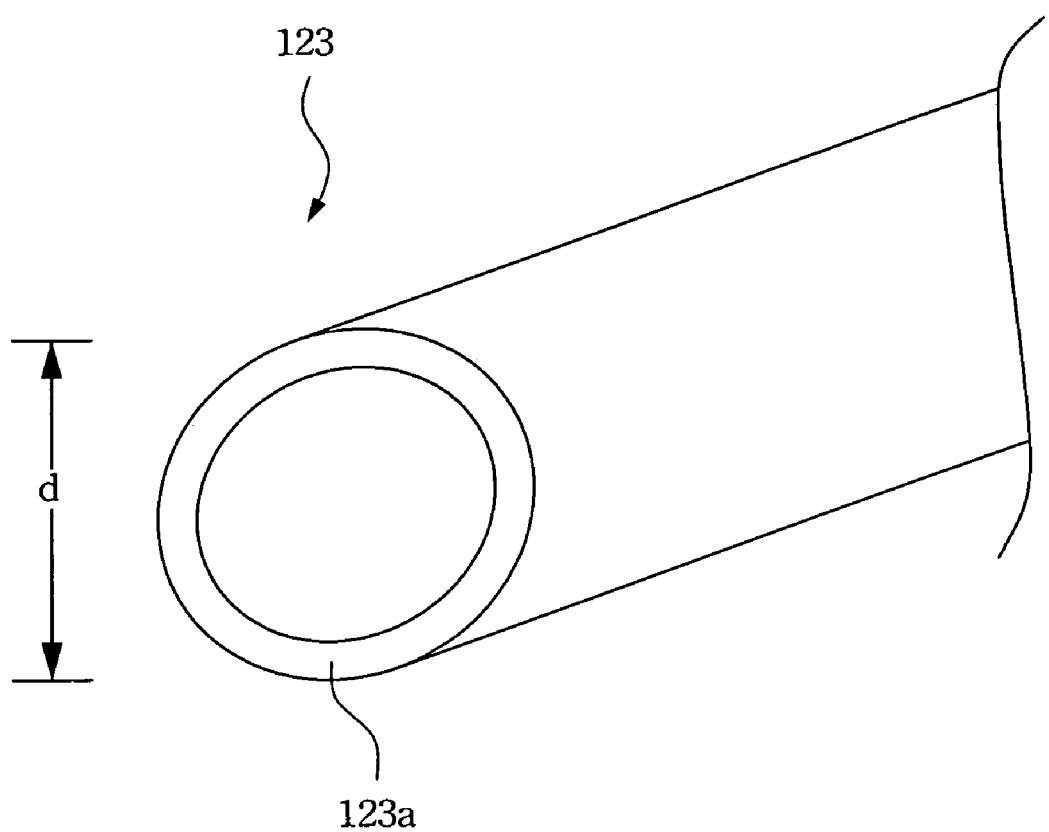
FIG. 7 illustrates a cross-sectional view of an electrically conductive fiber.

FIG. 7 illustrates a cross-sectional view of an electrically conductive fiber. Every electrically conductive yarn 120 consists of many electrically conductive fibers 123. In order to increase performance of the electrically conductive fibers 123, each fiber 123 is coated with an outer layer 123a of previous metallic materials (such as gold, sliver or platinum). In this embodiment, the fiber 123 has a diameter of 10~25 μm. Besides, when a whole bunch of fibers 123 are bent as wave shape (as illustrated in FIG. 1 and FIG. 2), fibers 123 would be broadly extended to have more contact areas for collecting vital signals.

Figure 8:
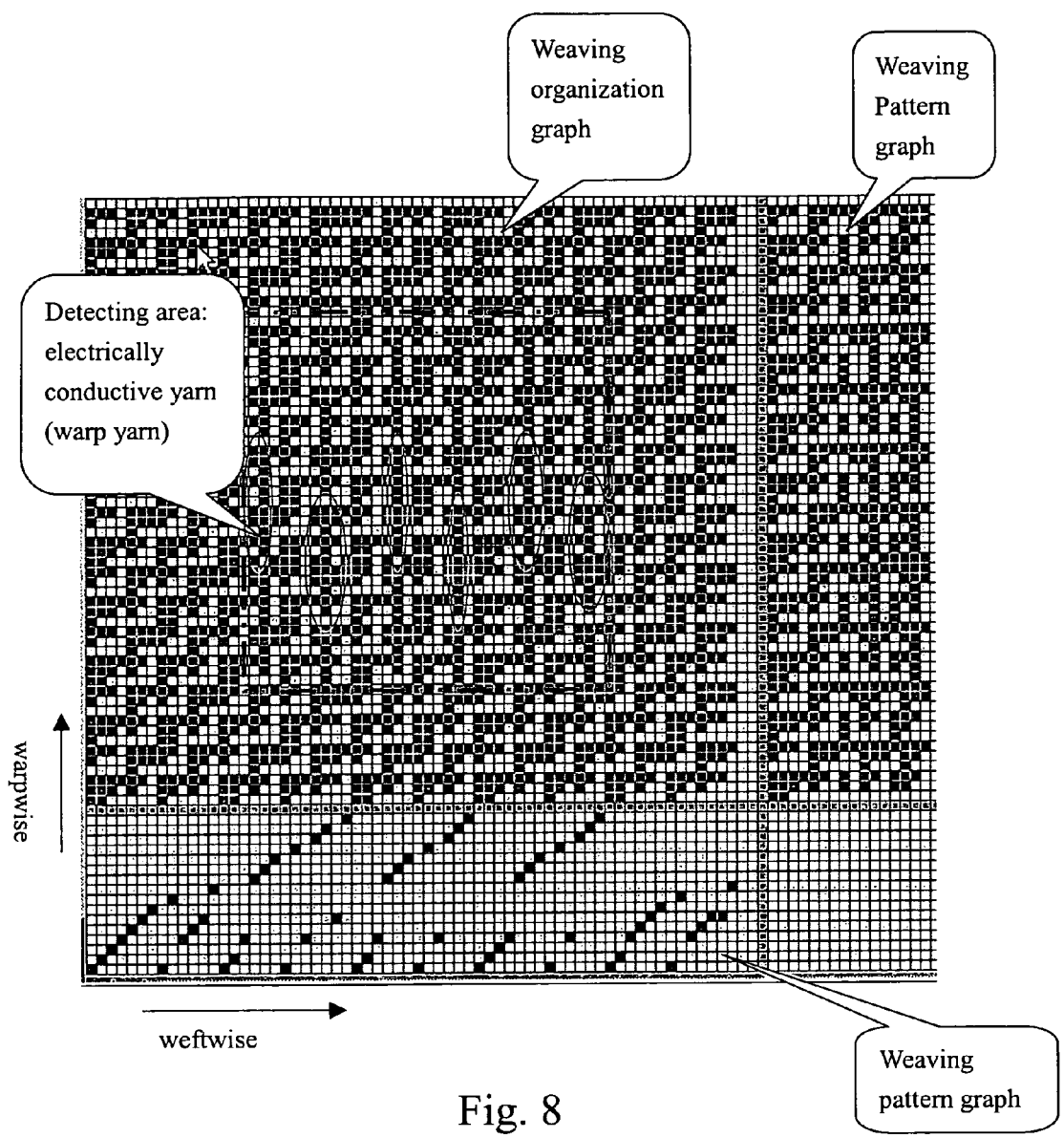
FIG. 8 illustrates weaving organization graphs and weaving pattern graphs for "one unit down and three units up" according to one preferred embodiment of this invention.

FIG. 8 illustrates weaving organization graphs and weaving pattern graphs for "one unit down and three units up" according to one preferred embodiment of this invention (darker dots are sticking-out warp yarns, and paler dots are sticking-out weft yarns). This graph has its weaving configurations as follows:

1. warp yarn: (A) silver-coated fiber 150d/72f
 (B) PET 150d/144f
 (C) elastic yarn 840d
 2. weft yarn: (A) PET 150d/72f
 3. warp yarn sequence: B2, C1, B14, A1, B5, A1, C1, B5, A1, B5, A1, B3, C1, B2, A1, B5, A1, B12, C1, B1
 4. weft yarn sequence: A1
 5. weaving sequence: 1. 2. 3. 4. 5. 6. 7. 1. 8. 4. 5. 6. 9. 1. 2. 4. 10. 11. 12. 1. 13. 4. 14. 15. 6. 16. 1. 2. 4. 10. 11. 12. 1. 13. 4. 14. 15. 16. 1. 2. 3. 4. 10. 11. 12. 1. 13. 4. 14. 15. 16. 1. 2. 4. 5. 6. 7. 1. 8. 4. 5. 6. 6. 9.

Figure 9:
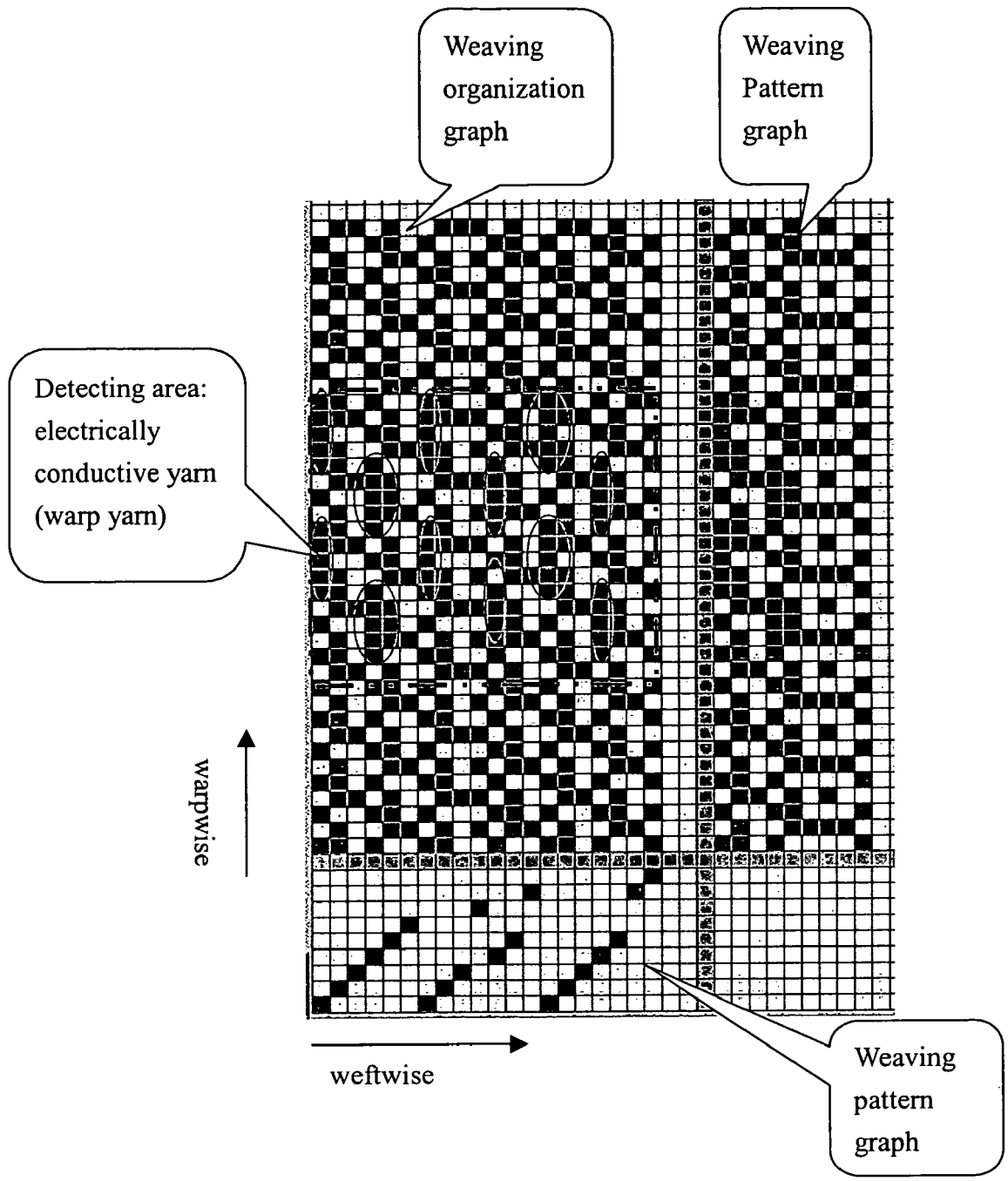
FIG. 9 illustrates weaving organization graphs and weaving pattern graphs for "one unit down and three units up" according to another preferred embodiment of this invention.

FIG. 9 illustrates weaving organization graphs and weaving pattern graphs for "one unit down and three units up" according to another preferred embodiment of this invention (darker dots are sticking-out warp yarns, and paler dots are sticking-out weft yarns). This graph has its weaving configurations as follows:

1. warp yarn:
 (A) silver-coated fiber 150d/72f
 (B) PET 150d/144f
 (C) elastic yarn 840d
 2. weft yarn: (A) PET 150d/72f
 3. warp yarn sequence: A1, B2, A1, B2, A1, B2, C1, A1, B2, A1, B2, A1, B2,
 4. weft yarn sequence: A1
 5. weaving sequence: 1. 2. 3. 4. 5. 6. 1. 2. 3. 7. 4. 5. 8. 1. 2. 3. 4. 5. 8. 9.

Figure 10:
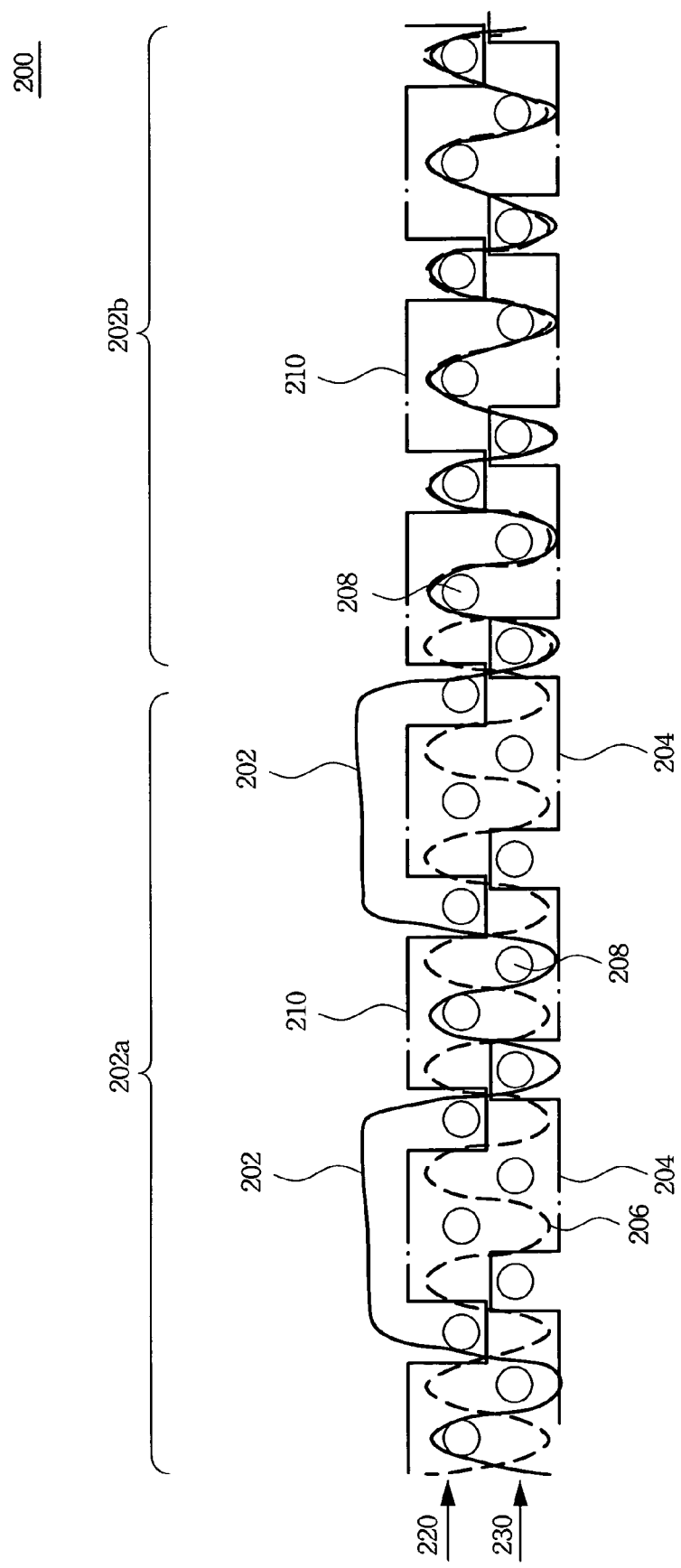
FIG. 10 illustrates a cross-sectional view of "one unit down and three units up" weaving way as in illustrated FIG. 9.

FIG. 10 illustrates a cross-sectional view of "one unit down and three units up" fabric as illustrated in FIG. 9. The electrically conductive yarn 202 is made from silver-coated fiber 150d/72f; the electrically insulating yarns (204, 210) are made from PET 150d/144f; the electrically insulating yarns 206 is made from PET 150d/144f or elastic yarn 840d. Double layers of fabric 200 include a first layer 220 and a second layer 230, and electrically conductive yarns are woven within thereof. The fabric 200 includes weftwise electrically insulating yarns 208, warpwise electrically insulating yarns (204, 206, 210) and warpwise electrically conductive yarns 202. The electrically conductive yarn 202 has a detecting section 202a and a transferring section 202b. The detecting section 120a is woven into the double layers of fabric 200 as a wave-shaped section. The detecting section 202a has all wave crests 120c sticking out of a surface of the first layer 220 for directly contacting human skins. The detecting section 202a has all wave troughs 120d woven within the first layer 220 and the second layer 230. The electrically conductive yarn 202 sticks out of a surface of the fabric 200 as the detecting section 120a while the electrically insulating yarn 204 sticks out of the opposite surface of the fabric 200. Because the electrically insulating yarn 204 is disposed between two adjacent electrically conductive yarns, the electrically conductive yarn 202 can be isolated from outer environment, and a third electrically insulating layer may not be necessary. The transferring section 202b is woven within the fabric 200, electrically isolated from outer environments and able to transfer vital signals to a measuring instrument (not illustrated in drawings).

In this preferred embodiment, the detecting section 202a is woven with the fabric 200 by "one unit down and three units up" (for the first layer 202). By "one unit down and three units up", it means that "after the detecting section 202a has its wave trough woven with one electrically insulating yarn 208, the detecting section 202a sticks out of the first layer 220, goes beyond three electrically insulating yarns 208, and then has its next wave trough woven with the fabric 200 again. "One unit down and three units up" is a better weaving way to control the sticking-out detecting section 202a to such a length that it will not be damaged due to being washed or in contact with human skins. However, it does not mean that other weaving ways is not proper for the present preferred embodiments, such as "one unit down and one units up" or "one unit down and five units up".

According to preferred embodiments discussed above, a fabric for detecting vital signals from human body is formed of electrically conductive yarns and electrically insulating yarns woven by a particular weaving way such that the detecting section of the electrically conductive yarns is able to collecting vital signals stably. Besides, the fabric is porous, soft, washable and bendable to makes its contact with human skins more comfortable.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A fabric for detecting vital signals from human body, comprising:
   a first layer of fabric formed of weft and warp electrically insulating years woven together; and
   electrically conductive yarns being woven in parallel with weft or warp electrically insulating yarns and interval-spaced from one another, each of the electrically conductive yarns has a wave-shaped detecting section, all wave crests of the wave-shaped detecting section being protruded out of a surface of the first layer of fabric, all wave troughs of the wave-shaped detecting section being woven within the layer of fabric,
   wherein each of electrically conductive yearns has its all wave crests misaligned in position with all wave troughs of its immediately adjacent electrically conductive yarn.

2. The fabric of claim 1, further comprising two second layers of fabric, which are disposed on an opposite surface of the first layer of fabric and formed of weft and warp electrically insulating yarns woven together.

3. The fabric of claim 2, wherein each of electrically conductive yearns has a transferring section woven with an intermediate layer of the three layers of fabric.

4. The fabric of claim 2, wherein any immediately adjacent two of electrically conductive yarns have the at least one electrically insulating yarn disposed therebetween.

5. The fabric of claim 2, wherein the electrically insulating yarns, which are in parallel with the electrically conductive yearns, have a larger linear elasticity than that of the electrically insulating yarns, which are not in parallel with the electrically conductive yarns.

6. The fabric of claim 2, wherein each of the electrically conductive yarns consists of a plurality of electrically conductive fibers with a diameter of 10-25 μm.

7. The fabric of claim 6, wherein each of the electrically conductive fibers comprises an outer coating of gold, silver or platinum.

8. The fabric of claim 2, wherein each of electrically conductive yarns has its any immediately adjacent two wave troughs disposed with three electrically insulating yarns therebetween.

9. The fabric of claim 1, further comprising a second layer of fabric formed of weft and warp electrically insulating yarns woven together and an electrically insulating layer, which both are disposed on an opposite surface of the first layer of fabric, the second layer of fabric is disposed between the first layer of fabric and the electrically insulating layer.

10. The fabric of claim 9, wherein each of electrically conductive yarns has a transferring section woven with the second layer of fabric.

11. The fabric of claim 9, wherein any immediately adjacent two of electrically conductive yearns have the at least one electrically insulating yarn disposed therebetween.

12. The fabric of claim 9, wherein the electrically insulating yarns, which are in parallel with the electrically conductive yarns, have a larger linear elasticity than that of the electrically insulating yarns, which are not in parallel with the electrically conductive yarns.

13. The fabric of claim 9, wherein each of the electrically conductive yarns consists of a plurality of electrically conductive fibers with a diameter of 10-25 μm.

14. The fabric of claim 13, wherein each of the electrically conductive yarns comprises an outer coating of gold, silver or platinum.

15. The fabric of claim 9, wherein each of electrically conductive yarns has its any immediately adjacent two wave troughs with three electrically insulating yarns disposed therebetween.

16. A fabric for detecting vital signals from human body, comprising:
   two layers of fabric each formed of weft and warp electrically insulating yarns woven together; and
   electrically conductive yarns being woven in parallel with weft or warp electrically insulating yarns and interval-spaced from one another, each of the electrically conductive yarns has a wave-shaped detecting section, all wave crests of the wave-shaped detecting section being protruded out of a surface of the two layers of fabric, all wave troughs of the wave-shaped detecting section being woven within the two layers of fabric,
   wherein each of electrically conductive yarns has its all wave crests misaligned in position with all wave crests of its immediately adjacent electrically conductive yarn, and each of electrically conductive yarns has its all wave troughs misaligned in position with all wave troughs of its immediately adjacent electrically conductive yarn.

17. The fabric of claim 16, wherein each of electrically conductive yarns has a transferring section woven within the two layers of fabric.

18. The fabric of claim 16, wherein any immediately adjacent two of electrically conductive yarns have the at least one electrically insulating yarn disposed therebetween.

19. The fabric of claim 16, wherein the electrically insulating yarns, which are in parallel with the electrically conductive yarns, have a larger linear elasticity than that of the electrically insulating yarns, which are not in parallel with the electrically conductive yarns.

20. The fabric of claim 16, wherein each of electrically conductive yarns has its any immediately adjacent two wave troughs disposed with three electrically insulating yarns therebetween.

* * * * *

UNITED STATES PATENT AND TRADEMARK OFFICE
CERTIFICATE OF CORRECTION

PATENT NO. : 7,828,019 B2
APPLICATION NO. : 12/228318
DATED : November 9, 2010
INVENTOR(S) : Chien-Lung Shen et al.

It is certified that error appears in the above-identified patent and that said Letters Patent is hereby corrected as shown below:

Col. 4, Line 44
 Insert --C1-- after B2, A1, B2, A1, B2,

Signed and Sealed this
Eighteenth Day of October, 2011

David J. Kappos
*Director of the United States Patent and Trademark Office*